(12) United States Patent
Styles et al.

(10) Patent No.: US 9,315,533 B2
(45) Date of Patent: Apr. 19, 2016

(54) LACTOSE CRYSTALLISATION

(75) Inventors: Anthony James Styles, Lichfield (NZ); Paul Stephenson, Porirua (NZ)

(73) Assignees: FONTERRA CO-OPERATIVE GROUP LIMITED, Auckland (NZ); AUERCON NEW ZEALAND LIMITED, Wellington (NZ)

( * ) Notice: Subject to any disclaimer, the term of this patent is extended or adjusted under 35 U.S.C. 154(b) by 63 days.

(21) Appl. No.: 13/878,031

(22) PCT Filed: Oct. 10, 2011

(86) PCT No.: PCT/NZ2011/000212
§ 371 (c)(1),
(2), (4) Date: Oct. 15, 2013

(87) PCT Pub. No.: WO2012/047122
PCT Pub. Date: Apr. 12, 2012

(65) Prior Publication Data
US 2014/0051850 A1     Feb. 20, 2014

Related U.S. Application Data

(60) Provisional application No. 61/391,021, filed on Oct. 7, 2010.

(51) Int. Cl.
| C07H 1/06 | (2006.01) |
| A23C 1/12 | (2006.01) |
| C13K 5/00 | (2006.01) |

(52) U.S. Cl.
CPC .. *C07H 1/06* (2013.01); *A23C 1/12* (2013.01); *C13K 5/00* (2013.01); *A23V 2002/00* (2013.01)

(58) Field of Classification Search
CPC .............. C07H 1/06; A23C 1/12; C13K 5/00; A23V 2002/00; A23V 2250/612
USPC .................................................... 536/123.13
See application file for complete search history.

(56) References Cited

U.S. PATENT DOCUMENTS

| 4,404,038 A | 9/1983 | Credoz et al. |
| 2003/0196957 A1 | 10/2003 | Henningfield et al. |
| 2011/0003355 A1* | 1/2011 | Clark et al. ................... 435/158 |

FOREIGN PATENT DOCUMENTS

| FR | 2 493 679 | 5/1982 |
| GB | 534214 | 3/1941 |

OTHER PUBLICATIONS

Dryden, J.W., "Crystal Clear. The story of the Lactose Company of New Zealand." pp. 64, 65, 70, 110, 116, 123 and 131.
McLeod, J., (2007) PhD Thesis. Nucleation and Growth of Alpha Lactose Monohydrate, pp. 1.3 and 1.4.
"Production and uses of lactose" in Advanced Dairy Chemistry. (3rd ed, McSweenew and Fox (eds) Springer Publishers, New York).pp. 1-6.
Vu et al., "Dynamic Modelling and Simulation of Lactose Cooling Crystallisation: from Batch and Semi-Batch to Continuous Operations", (2005) European Symposium on Computer Aided Process Engineering.
International Search Report mailed Jan. 13, 2012 in Application No. PCT/NZ2011/000212, filed Oct. 10, 2011.
EPO Communication Pursuant to Rule 114(2) Third Party Observation for Application No. EP20110830982 dated Nov. 23, 2015.
Bennett, Richard C., "Crystallizer Selection and Design", Chapter 5 of Handbook of Industrial Crystallization (Second Edition), Edited by Allan S. Myerson, 2002, Elsevier Inc., pp. 115-140.
McLeod, Jeremy, "Nucleation and Growth of Alpha Lactose Monohydrate", A Thesis presented in partial fulfilment of the requirements for the degree of Doctor of Philosophy in Process Engineering at Massey University, 2007.
Krömker, Volker, "Zusammnensetzung der Milch", in "Kurzes Lehrbuch Milchkunde and Milchhygiene", Parey, Dec. 6, 2006, pp. 99-100.

* cited by examiner

*Primary Examiner* — Mark Shibuya
*Assistant Examiner* — Yih-Horng Shiao
(74) *Attorney, Agent, or Firm* — Knobbe, Martens, Olson & Bear LLP

(57) ABSTRACT

The invention relates to a method of crystallizing lactose from a lactose-containing liquid comprising the steps of providing a lactose-containing liquid comprising less than 80% by weight total solids, providing an evaporator system that comprises a heat exchanger and an evaporation vessel, the heat exchanger comprising a tube or tubes that define a flowpath having an inlet and an outlet, heating the lactose-containing liquid in the heat exchanger to about 50 to about 90° C. such that the lactose-containing liquid passes along the flowpath by forced circulation or thermo-siphoning, concentrating the lactose-containing liquid in the evaporation vessel, to generate crystallized lactose in the lactose-containing liquid in the evaporator system.

23 Claims, 2 Drawing Sheets

LACTOSE CRYSTALLISATION

FIELD OF THE INVENTION

The present invention relates to a method for producing crystallised lactose.

BACKGROUND TO THE INVENTION

When in solution, lactose exists in equilibrium between two isomeric forms: α-lactose and β-lactose. α-lactose is the desired form. The solubility of lactose (in either form) decreases as the temperature is lowered.

Crystallisation of a lactose solution produces crystals of α-lactose monohydrate (ALM). As ALM crystals are formed β-lactose coverts to α-lactose in the solution to maintain the equilibrium between these two isomers.

The aim of a crystallisation process is to produce
crystals in high yield, and
high purity.

Methods for making lactose have been reported, such as in U.S. Pat. No. 4,404,038. Such methods suffer from one or more technical limitations such as the quality of the input, depositions and hygiene, viscosity, heat transfer efficiency, quality of crystallisation and particle size distribution, and loss of fines, leading to low efficiency and yield (see Chapter 4 of Advanced Dairy Chemistry, volume 3 [ed. McSweeney and Fox, Springer Science, 2009]).

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

It is an object of the present invention to provide a method of producing lactose which at least provides the public with a useful choice.

Other objects of the invention may become apparent from the following description which is given by way of example only.

SUMMARY OF THE INVENTION

In one aspect the invention relates to a method of crystallising lactose from a lactose-containing liquid comprising
providing a lactose-containing liquid comprising less than 80% by weight total solids,
providing an evaporator system that comprises a rising film or flooded tube heat exchanger and an evaporation vessel,
heating the lactose-containing liquid in the rising film or flooded tube heat exchanger to about 50 to about 90° C.,
concentrating the lactose-containing liquid in the evaporation vessel,
to generate crystallised lactose in the lactose-containing liquid in the evaporator system.

In a further aspect the invention relates to a method of crystallising lactose from a lactose-containing liquid comprising
providing a lactose-containing liquid comprising less than 80% by weight total solids,
providing an evaporator system that comprises a heat exchanger and an evaporation vessel, the heat exchanger comprising a tube or tubes that define a flowpath having an inlet and an outlet,
heating the lactose-containing liquid in the heat exchanger to about 50 to about 90° C. such that the lactose-containing liquid passes along the flowpath by forced circulation or thermo-siphoning,
concentrating the lactose-containing liquid in the evaporation vessel,
to generate crystallised lactose in the lactose-containing liquid in the evaporator system.

In a further aspect the invention relates to a method of crystallising lactose from a lactose-containing liquid comprising
causing a heat exchange assisted evaporation of the lactose-containing liquid by heating the lactose-containing liquid in a heat exchanger to about 50 to about 90° C.,
wherein the heat exchange is into the lactose-containing liquid when moving sufficiently to at least substantially entrain the lactose that has, or is being, crystallised out.

The following embodiments may relate to any of the above aspects.

In some embodiments the volume of liquid in the crystallising evaporator is at least half the hourly throughput volume of the liquid input into the system.

In some embodiments the ratio of the crystallising evaporator liquid volume to the hourly throughput volume of the liquid input to the system is at least 1:2.

In some embodiments the average residence time of the lactose-containing liquid in the crystallising evaporator is at least 30 min.

In some embodiments the lactose-containing liquid passes through the heat exchanger with a turbulent flow.

In some embodiments the lactose-containing liquid passes through the heat exchanger by forced circulation or thermo-siphoning.

In some embodiments multiple crystallising evaporators are used in series. Preferably 2, 3, or 4 crystallising evaporators are employed. More preferably 2 or 3 crystallising evaporators are used in series.

In some embodiments the crystallised lactose-containing fluid exiting the crystallising evaporator of the present invention is of a consistent nature. Preferably the crystals in the crystallised lactose-containing fluid exiting the crystallising evaporator are homogeneously distributed within the lactose-containing fluid exiting the crystallising evaporator.

In some embodiments, at least 90% of the lactose crystals by weight eluting from the outlet of the crystallising evaporator have a particle size of at least 90, 100, 110, 120, 130, 140, 150, 160, 170, 180, 190 or 200 microns in diameter.

In some embodiments, at least 50% of the lactose crystals by weight eluting from the outlet of the crystallising evaporator have a particle size of at least 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 microns in diameter.

In some embodiments, at least 10% of the lactose crystals by weight eluting from the outlet of the crystallising evaporator have a particle size of at least 500, 550, 600, 650, 700, 750, 800, 850, 900, 950 or 1,000 microns in diameter.

In some embodiments the crystallised concentrated lactose-containing liquid has a dissolved lactose content from about 1 to about 217 grams per 100 grams of water and a total solids content from about 58 to 80% by weight.

In some embodiments the evaporation vessel has an inlet to receive heated lactose-containing liquid from the heat exchanger, and an outlet to re-circulate the lactose-containing liquid to the heat exchanger.

In some embodiments the heat exchanger comprises a tube or tubes that define a flowpath having an inlet for introducing lactose-containing liquid and an outlet for the heated lactose-containing liquid.

In some embodiments the lactose-containing liquid is recirculated between the heat exchanger and the evaporation vessel.

In some embodiments the heat exchanger is a rising film or flooded tube heat exchanger.

In some embodiments the lactose-containing liquid is heated in the heat exchanger to a temperature of about 50 to about 90° C.

In some embodiments the heat exchanger outlet is above the heat exchanger inlet and connected to the inlet by a flowpath that rises from the inlet to the outlet.

In some embodiments a portion of the lactose containing liquid that is heated in the heat exchanger is converted to vapour and both the vapour and lactose-containing liquid pass along the flowpath with a turbulent flow.

In some embodiments the provided lactose-containing liquid comprises from about 5 to about 62% by weight total solids, In some embodiments the evaporator system heats the lactose-containing liquid to about 50, 55, 60, 65, 70, 75, 80, 85 or 90° C.

In some embodiments the evaporator system heats the lactose-containing liquid to about 50° C. to about 90° C.

In some embodiments the evaporator system heats the lactose-containing liquid to about 65° C. to about 70° C.

In some embodiments the temperature of the evaporator system is controlled by a vapour chest and condenser.

In some embodiments the total solids content of the crystallised lactose-containing liquid is 58, 62, 68, 66, 70, 74, 78, or 80% by weight total solids.

In some embodiments the total solids content of the crystallised lactose-containing liquid is from about 58 to about 72% by weight.

In some embodiments the average residence time in the evaporative system is about 1, 2, 3, 4 or 5 hours.

In some embodiments the provided lactose-containing liquid contains from about 5, 10, 15, 20, 25, 30, 35, 40, 45, 50, 55, 60, or 62% by weight total solids.

In some embodiments the provided lactose-containing liquid contains from about 58 to about 62% by weight total solids.

In some embodiments the lactose-containing liquid comprises from about 5 to about 24% by weight total solids, that is further concentrated to about 55 to about 62% by weight total solids for transfer to the crystallising evaporator. Preferably the further concentration is performed by an evaporator. More preferably the evaporator is a falling film evaporator.

In some embodiments, after sufficient residence time has occurred in the evaporation vessel, a portion of concentrated lactose-containing liquid is recirculated to the heat exchanger and the remainder of the concentrated lactose-containing liquid is transferred to a cooling crystalliser.

In some embodiments, after sufficient lactose crystal growth has occurred in the evaporation system, the concentrated lactose-containing liquid, having a total solids content of from about 58 to about 80% by weight, is transferred to a cooling crystalliser.

In some embodiments the cooling crystalliser produces a mother liquor having a total solids content of about 35, 36, 37, 38, 39, 40, 41, 42, 43, 44, 45, 46, 47, 48, 49, 50, 51, 52, 53, 54 or 55% by weight.

In some embodiments the cooling crystalliser produces a mother liquor having a total solids content of from about 35 to 55% by weight.

In some embodiments the concentrated lactose-containing liquid that is transferred to a cooling crystalliser is classified by particle size.

In some embodiments a hydrocyclone is used to classify the concentrated lactose-containing liquid into the liquid that is recirculated to the evaporator system and liquid that is transferred to a cooling crystalliser.

In some embodiments the hydrocyclone classifies the crystallised lactose-containing liquid into two streams of lactose-containing liquid, the first stream having lactose crystals of larger average size than the second stream, and wherein the first stream is transferred to a cooling crystalliser and the second stream is recirculated to the crystallising evaporator.

In some embodiments sufficient crystal growth occurs once the mean crystal size is greater than about 100 Preferably the first stream has a mean crystal size greater than about 100 Preferably the second stream has a mean crystal size less than about 100μ.

In some embodiments the crystallised lactose-containing liquid is recirculated between the heat exchanger and the evaporation vessel until the lactose-containing liquid reaches a total solids content of about 58, 60, 65, 70, 75 or 80% by weight.

In some embodiments the concentrated lactose-containing liquid is recirculated between the evaporator system and a crystal growth tank until the lactose-containing liquid reaches a total solids content of from about 58 to about 80% by weight.

In some embodiments the final temperature of the cooling crystalliser is about 8, 9, 10, 11, 12, 13, 14, 15, 16, 17, 18, 19, 20, 21, 22, 23, 24 or 25° C.

In some embodiments the final temperature of the cooling crystalliser is from about 8 to 25° C.

In some embodiments the crystallised lactose containing liquid remains in the crystallising tanks for about 15, 16, 17, 18, 19, 20, 21, 22, 23, 24, 25, 26, 27, 28, 29 or 30 hours.

In some embodiments the crystallised lactose containing liquid remains in the crystallising tanks from about 10 to about 72 hours.

In some embodiments the crystallised lactose is separated from the mother liquor.

In some embodiments a decanter centrifuge is used to separate the crystallised lactose from the mother liquor to produce a lactose crystal rich stream.

In some embodiments the lactose crystals are subsequently washed using water.

In some embodiments the lactose crystals are removed from the wash water using a centrifuge.

In some embodiments the lactose crystals are further purified.

In some embodiments the lactose crystals are processed by secondary crystallisation.

In some embodiments the lactose crystals are dried using hot air.

In some embodiments at least 95% by weight of the lactose crystals are alpha-lactose monohydrate. Preferably at least 99% by weight of the lactose crystals are alpha-lactose monohydrate.

In some embodiments the dried product comprises greater than 99% by weight total solids.

Other aspects of the invention may become apparent from the following description which is given by way of example only and with reference to the accompanying drawings.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting statements in this specification which include that term, the features, prefaced by that term in each statement or claim, all need to be present but other features can also be present. Related terms such as "comprise" and "comprised" are to be interpreted in the same manner.

BRIEF DESCRIPTION OF THE DRAWINGS

The invention will now be described by way of example only and with reference to the drawings in which.

DETAILED DESCRIPTION OF THE INVENTION

Figure 1:
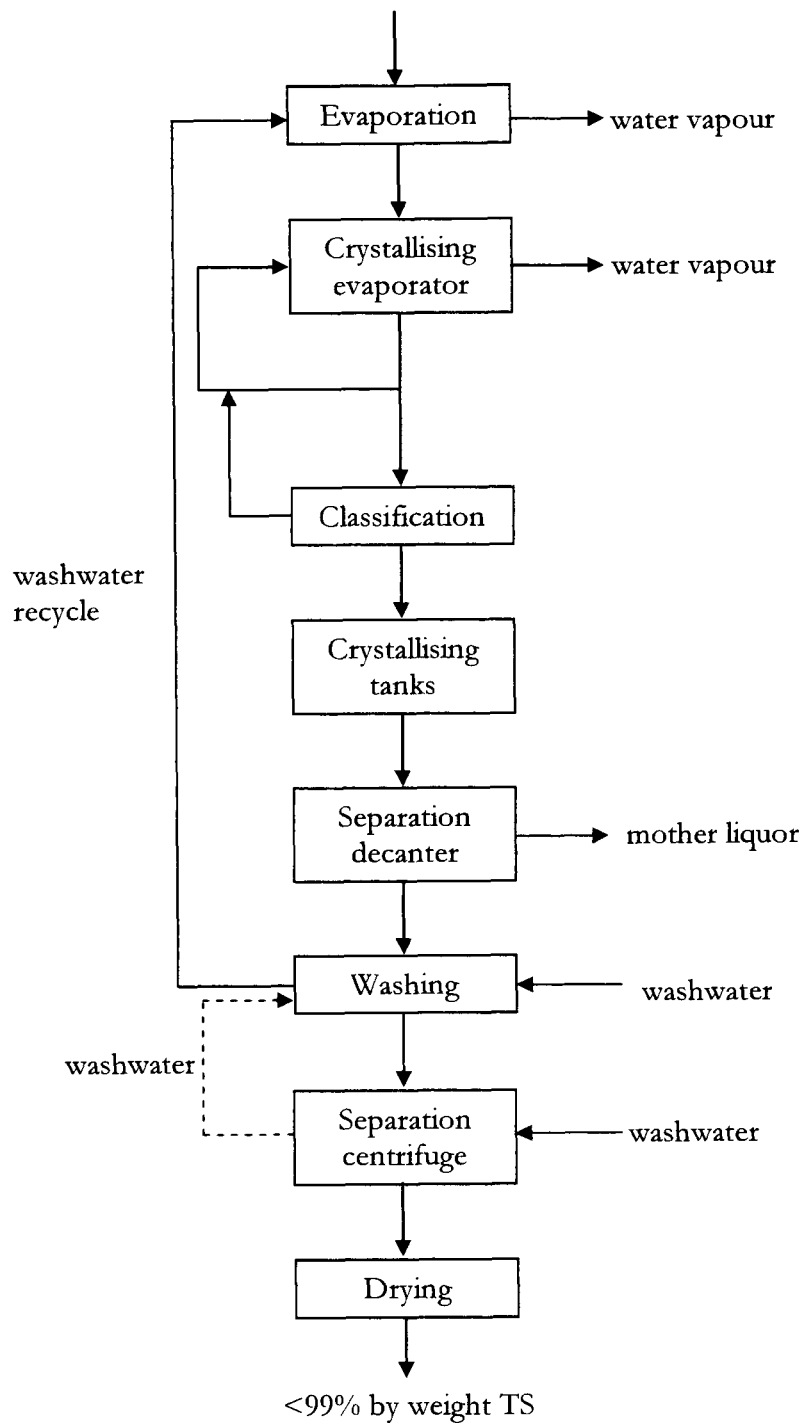
FIG. 1 shows a process flow diagram of the process for producing crystallised lactose powder.

The invention further relates to a method of crystallising lactose from a lactose-containing liquid comprising
providing a lactose-containing liquid comprising less than 80% by weight total solids,
providing an evaporator system that comprises a rising film or flooded tube heat exchanger and an evaporation vessel,
heating the lactose-containing liquid in the rising film or flooded tube heat exchanger to about 50 to about 90° C.,
concentrating the lactose-containing liquid in the evaporation vessel,
to generate crystallised lactose in the lactose-containing liquid in the evaporator system.

The invention further relates to a method of crystallising lactose from a lactose-containing liquid comprising
providing a lactose-containing liquid comprising less than 80% by weight total solids,
providing an evaporator system that comprises a heat exchanger and an evaporation vessel, the heat exchanger comprising a tube or tubes that define a flowpath having an inlet and an outlet,
heating the lactose-containing liquid in the heat exchanger to about 50 to about 90° C. such that the lactose-containing liquid passes along the flowpath by forced circulation or thermo-siphoning,
concentrating the lactose-containing liquid in the evaporation vessel,
to generate crystallised lactose in the lactose-containing liquid in the evaporator system.

The invention further relates to a method of crystallising lactose from a lactose-containing liquid comprising
providing a lactose-containing liquid comprising less than 80% by weight total solids,
providing an evaporator system that comprises a heat exchanger and an evaporation vessel,
heating the lactose-containing liquid in the heat exchanger to about 50 to about 90° C., concentrating the lactose-containing liquid in the evaporation vessel,
to generate crystallised lactose in the lactose-containing liquid in the evaporator system and wherein the run time of the evaporator system prior to any need for de-fouling on that side of the heat exchanger that contains the lactose-containing liquid is at least 10 hours.

The invention further relates to a method of crystallising lactose from a lactose-containing liquid comprising
causing a heat exchange assisted evaporation of the lactose-containing liquid by heating the lactose-containing liquid in a heat exchanger to about 50 to about 90° C.,
wherein the heat exchange is into the lactose-containing liquid when moving sufficiently to at least substantially entrain the lactose that has, or is being, crystallised out.

The invention further relates to a method of crystallising lactose with increased efficiency.

1. Lactose-Containing Liquid

The lactose-containing liquid for use in the invention is obtained from mammalian milk. It should be appreciated that any fraction or milk derivative can be utilised in the invention provided it contains lactose.

In some embodiments, the lactose-containing liquid may be derived from any mammalian milk including but not limited to bovine, sheep, goat, pig, mouse, water buffalo, camel, yak, horse, donkey, llama or human milk fat, with bovine milk being a preferred source.

In some embodiments the mammalian milk source is processed to remove protein and fat prior to being used in the inventive process.

By way of example, the lactose-containing liquid may be generated from upstream milk processes, such as cheese manufacture or casein manufacture that produce a permeate. Examples of upstream milk processes include the production of cheese whey, rennet (sweet) whey, or ultrafiltration of skim or raw milk. After ultrafiltration of whey protein the protein is retained in the whey retentate and the whey permeate contains lactose and minerals, since lactose and minerals pass though the ultrafiltration membrane.

The lactose source (e.g. permeate from upstream dairy processing) may then be processed by one or more filtration steps and may include one or more concentration steps.

In some embodiments the lactose-containing liquid is the permeate resulting from filtration of whole milk, recombined, powdered or fresh skim milk, recombined or reconstituted whole or skim milk powder, skim milk concentrate, skim milk retentate, concentrated milk, ultrafiltered milk retentate, milk protein concentrate (MPC), milk protein isolate (MPI), calcium depleted milk protein concentrate (MPC), low fat milk, low fat milk protein concentrate (MPC), casein, caseinate, milk fat, cream, butter, anhydrous milk fat (AMF), buttermilk, colostrum, a colostrum fraction, colostrum protein concentrate (CPC), colostrum whey, whey (including sweet whey, lactic acid whey, mineral acid whey, or reconstituted whey powder), whey protein isolate (WPI), whey protein concentrate (WPC), a composition derived from any milk or colostrum processing stream, a composition derived from the retentate or permeate obtained by ultrafiltration or microfiltration of any milk or colostrum processing stream. It should be understood that the source of these derivatives may be milk or colostrum or a combination thereof.

In some embodiments the permeate is concentrated by removing water. Any concentration process can be used to effect this, such as by reverse osmosis or evaporation. Both reverse osmosis and evaporation may be used.

For example, in some embodiments the permeate is concentrated by using reverse osmosis.

In some embodiments the permeate after concentration by reverse osmosis comprises at least about 10, 11, 12, 13, 14, 15, 16, 17, 18, 19, 20, 21, 22, 23, 24, 25, 26, 27, 28, 29 or 30% by weight total solids and useful ranges may be selected between any of these values (for example, about 10 to about 30, about 15 to about 30, about 20 to about 30, about 25 to about 30, about 10 to about 20, about 10 to about 25, about 10 to about 15, about 15 to about 25, about 15 to about 20, about 18 to about 30, about 18 to about 25, about 18 to about 20 or 16 to about 22% by weight total solids).

In some embodiments the permeate is concentrated by evaporation. The removal of water is limited by the need to be able to use temperature to control supersaturation and the need to maintain the permeate in a liquid state that can be pumped and separated from the crystals. Evaporation for the purpose of concentration can be carried out by any evaporative process known, such as the use of evaporators such as a falling film evaporator, rising film evaporator, plate evaporator, or multiple effect evaporator.

In some embodiments the permeate after concentration by evaporation comprises at least about 40, 42, 44, 46, 48, 50, 52, 54, 56, 58, 60, 62, 64, 66, 68, 70, 72, 74, 76 or 78% by weight total solids and useful ranges may be selected between any of these values (for example, about 40 to about 78, about 40 to about 70, about 40 to about 62, about 46 to about 78, about 46 to about 70, about 46 to about 62, about 58 to about 78, about 58 to about 70 or about 58 to about 62% by weight total solids).

In some embodiments the evaporation temperature is about 50, 52, 54, 56, 58, 60, 62, 64, 66, 68, 70, 72, 74, 76, 78, 80, 82, 84, 86, 88, or 90° C. and useful ranges may be selected between any of these values (for example, about 50 to about 90, about 50 to about 80, about 50 to about 76, about 50 to about 70, about 50 to about 66, about 56 to about 90, about 56 to about 80, about 56 to about 76, about 56 to about 70, about 56 to about 66, about 60 to about 90, about 60 to about 80, about 60 to about 76, about 60 to about 66, about 66 to about 80, about 66 to about 76, about 66 to about 70, about 74 to about 90, about 74 to about 84 or 74 to about 80° C.).

2. Crystallisation

Figure 2:
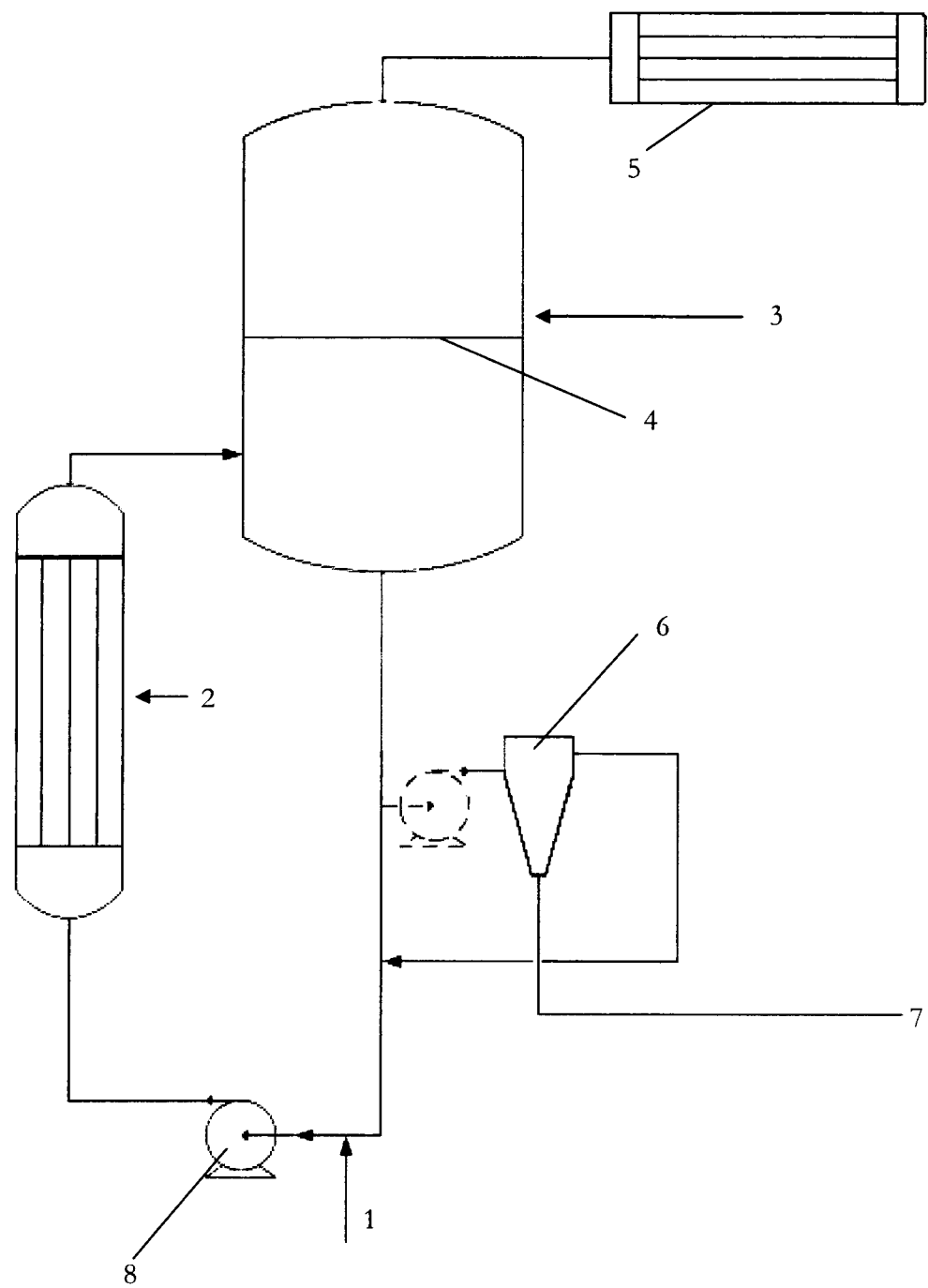
FIG. 2 shows the arrangement of a crystallising evaporator that comprises a flooded tube heat exchanger.

Crystallisation of the lactose-containing liquid is carried out in the evaporator system. As seen in FIG. 2 the evaporator system consists of a heat exchanger 2 and an evaporation vessel 3. This vessel is the point where vapour and liquid 4 are separated. Lactose-containing liquid 1 is continuously fed into the evaporator system 1 and crystal slurry is removed out to a cooling process 7.

Control of crystal size in this evaporator is achieved using a combination of factors such as the recirculation rate, the use of a hydrocyclone, residence time in the evaporation vessel 3 (controlled by varying the level 4), and temperature to vary the solubility and therefore the supersaturation.

In some embodiments the crystallised concentrated lactose-containing liquid has a dissolved lactose content from about 1 to about 217 grams per 100 grams of water and a total solids content from about 58 to 80% by weight.

The volume of liquid in the evaporating crystalliser is important. For example, in some embodiments the volume of liquid in the evaporator system is at least half the hourly throughput volume of the liquid input into the system. Put another way, the ratio of the evaporation system liquid volume to the hourly throughput volume of the liquid input to the system is at least 1:2. The volume of liquid in the evaporating crystalliser is directly implied by the "average liquid residence time" being at least 30 min In some embodiments the circulation of the lactose-containing liquid in the heat exchanger and separator vessel is driven using an axial flow pump 8. Other pumps could be used, for example, a centrifugal pump. In some embodiments the agitation or turbulence provided by this pump plays an important role in the nucleation of the lactose crystals.

The heat exchanger used in the inventive process allows initialisation of crystallisation in the lactose-containing liquid in the evaporator system and maintains the lactose supersaturation as crystals are formed and grow. The heat exchanger is of a type that operates using forced circulation or thermo-siphoning.

In some embodiments the heat exchanger is a rising film or flooded tube heat exchanger.

Most prior art methods for producing crystallised lactose do not grow crystals in the evaporator, but in cooling crystallising tanks. This has the effect of limiting the amount of total solids that the liquid can be concentrated to. This is because increasing the total solids content in the evaporator causes fouling and uncontrolled crystal growth (showering).

The invention relates to a method of using a heat exchanger, such as a rising film or flooded tube heat exchanger, that allows controlled growth of crystals in the evaporator. An advantage of this method is that it allows a higher solids content to be achieved.

Some falling film finishing evaporators operate at high temperature and can produce high total solids, however, they do not produce crystals. This high solids content is not fed to traditional crystallising tanks because of the high risk of showering leading to creation of many small crystals that get lost from the yield in separation from mother liquor and washing.

Additionally, at high total solids the permeate stream in a falling film evaporator does not distribute evenly. This results in localised concentration and uncontrolled crystallisation leading to fouling of the evaporator heat exchanger tubes, burning on and blocking the tubes and restriction of the flow in the evaporator heat exchanger.

With a rising film or flooded tube heat exchanger the majority of the tube (of the heat exchanger) is filled with liquid. The liquid is in a constant state of movement owing to recirculation through the heat exchanger by thermal activity or a pump. This results in both a homogenous concentration of solids, and solids that do not localise to the surface of the heat exchanger, as occurs at high solids (i.e. >60%) concentration with falling film heat exchangers.

Additionally, vapourisation occurs at the top of the heat exchanger in the case of a rising film heat exchanger, and off the top of the vessel in the case of the flooded tube heat exchanger, and therefore this is where most of the localised lactose concentration occurs. However, with a falling film heat exchanger concentration of the vapour occurs throughout the length of the tube of the heat exchanger (as opposed to the top of the heat exchanger tube) leading to crystal nucleation and increased fouling of the heat exchanger.

An advantage of using the rising film or flooded tube heat exchanger is that it allows crystallisation to be initiated in the heat exchanger 2 and crystallising vessel 3, which allows production of liquids with higher total solids (for example, up to 80% by weight TS). This leads to an increase in yield from prior art processes of 60 to 65% by weight to approximately about 70 to about 80% by weight. This means less lactose is lost in the mother liquor.

In some embodiments the temperature within the crystallising evaporator is maintained at from about 50° C. to about 90° C. and useful ranges may be selected between any of these values (for example, about 50 to about 90, about 50 to about 80, about 50 to about 76, about 50 to about 70, about 50 to about 66, about 56 to about 90, about 56 to about 80, about 56 to about 76, about 56 to about 70, about 56 to about 66, about 60 to about 90, about 60 to about 80, about 60 to about 76, about 60 to about 66, about 66 to about 80, about 66 to about 76, about 66 to about 70, about 74 to about 90, about 74 to about 84 or 74 to about 80° C.).

In some embodiments the operating temperature of the crystallising evaporator is controlled by a vapour chest and condenser 5.

In some embodiments the concentrated lactose-containing liquid that is transferred to a cooling crystalliser is classified by particle size.

In some embodiments a hydrocyclone 6 is used to classify the concentrated lactose-containing liquid into the liquid that is recirculated to the crystallising evaporator and the liquid that is transferred to a cooling crystalliser.

In some embodiments the concentrated product is pumped into the hydro-cyclones and using centripetal force the larger crystals are separated from the smaller ones. The larger crystals are sent to the cooling crystallisers, with the smaller ones being retained in the process to allow them further time for growth. The use of the hydrocyclones allows the operation of a continuous process and increases the mean particle size produced.

In some embodiments the hydrocyclone classifies the concentrated lactose-containing liquid into two streams of liquid, the first stream having lactose crystals of larger average size than the second stream, and wherein the first stream is transferred to a cooling crystalliser and the second stream is recirculated to the crystallising evaporator.

In some embodiments, after sufficient crystal growth has occurred in the crystal growth tank, a portion of concentrated lactose-containing liquid is recirculated to the heat exchanger and the remainder of the concentrated lactose-containing liquid is transferred to a cooling crystalliser.

A further advantage of this invention is because of the controlled nature of the crystal growth in the crystallising evaporator the nature of the crystals into and out of the cooling crystallisers are of consistent nature (size and distribution) throughout the run. This allows good control in the downstream processing (washing, drying and packaging) of the lactose crystals, whereas with prior art methods, quite large variation in particle nature can occur between cooling crystalliser batches with even small changes of input concentrate composition, solids content and temperature.

Methods for measuring particle size are known in the art. For example, as performed using the Malvern instrumentation.

In some embodiments, at least 90% of the lactose crystals by weight eluting from the crystallising evaporator's outlet (i.e. to the cooling crystalliser) have a particle size of at least 90, 100, 110, 120, 130, 140, 150, 160, 170, 180, 190 or 200 microns in diameter, and useful ranges may be selected between any of these values (for example, about 90 to about 200, about 90 to about 150, about 90 to about 12, about 100 to about 200, about 100 to about 160, about 140 to about 200, about 140 to about 180 microns in diameter).

In some embodiments, at least 50% of the lactose crystals by weight eluting from the outlet of the crystallising evaporator have a particle size of at least 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 microns in diameter, and useful ranges may be selected between any of these values (for example, about 200 to about 500, about 200 to about 450, about 200 to about 350, about 200 to about 350, about 200 to about 300, about 250 to about 500, about 250 to about 320, about 280 to about 500, about 280 to about 330 microns in diameter).

In some embodiments, at least 10% of the lactose crystals by weight eluting from the outlet of the crystallising evaporator have a particle size of at least 500, 550, 600, 650, 700, 750, 800, 850, 900, 950 or 1,000 microns in diameter, and useful ranges may be selected between any of these values (for example, about 500 to about 1,000, about 500 to about 800, about 500 to about 700, about 500 to about 600, about 500 to about 550, about 550 to about 1,000, about 550 to about 800, about 550 to about 700, about 600 to about 1,000, about 600 to about 800, about 600 to about 700, about 650 to about 1,000, about 650 to about 800, about 650 to about 750 and about 700 to about 1000).

The cooling stage of the crystallisation process lowers the solubility of the lactose driving crystal growth and increasing the yield. In both processes the crystals that leave the evaporative crystallisation process are close to their final size. The large population of crystals means that the remaining crystallisation process contributes only a very small percentage to the final individual crystal size.

In some embodiments the concentrated lactose-containing liquid is recirculated between the crystallising evaporator and the crystal growth tank until the supersaturated lactose-containing liquid reaches a total solids content of from about 58, 60, 62, 64, 66, 68, 70, 72, 74, 76, 78 or 80% by weight.

In some embodiments the final temperature of the cooling crystalliser is from about 8, 9, 10, 11, 12, 13, 14, 15, 16, 17, 18, 19, 20, 21, 22, 23, 24 to 25° C., and useful ranges may be selected between any of these values (for example, about 8 to about 25, about 8 to about 20, about 8 to about 18, about 10 to about 25, about 10 to about 22, about 10 to about 20, about 12 to about 25, about 12 to about 23, about 12 to about 20, about 12 to about 18, about 15 to about 25, about 15 to about 20 or about 18 to about 25° C.).

Another advantage of using a flooded tube evaporator is that it reduces the frequency of cleaning required. For example, flooded tube evaporators can be operated for a number of weeks before cleaning is required.

In some embodiments the lactose crystallisation system of the present invention comprises multiple crystallising evaporators. In some aspects the provision of multiple crystallising evaporators replaces the need for standard evaporators.

In some embodiments, where multiple crystallising evaporators are used, 2, 3 or 4 crystallising evaporators are thermally connected in series. More preferably, 2 or 3 crystallising evaporators are connected in series. When connected in series, the product vapour from one evaporator condenses in the heater of the next evaporator. The lactose-containing liquid is fed into all evaporators in parallel. In each evaporator the total solids content of the lactose-containing liquid rises from about 50% to about 80%.

The benefit of the multiple evaporator system includes improved thermal efficiency over a single crystallising evaporator. The multiple evaporator system can also combine two separate process steps namely, one evaporation step to increase the total solids in the lactose-containing liquid from about 45 to about 65% with an otherwise separate single crystallising evaporator process step.

In some embodiments further processing steps are required, such as those known in the art to produce pharmaceutical and refined edible lactose.

3. Crystal Separation

Once the cooling process is complete the lactose crystals are separated from the remaining solution. In some embodiments a decanter centrifuge is used to separate the crystallised lactose from the mother liquor to produce a lactose crystal rich stream.

A slurry of mother liquor and crystals is pumped from the crystallisers into the centrifuge and the crystals are spun off. The mother liquor is discharged and the crystals move forward in the process. It is at this point that fine crystals become a problem as they are hard to separate from the mother liquor and are lost from the process.

An advantage of the inventive process relates to the improved value of the by-product, mother liquor, without further processing. Typically, in the present process there is less volume of mother liquor produced for the same amount of feed permeate stream and the mother liquor is of higher total solids concentration, at least 35% by weight total solids resulting in the following advantages.

Lower transport costs for the mother liquor.

A better suited mother liquor for animal feed. As the mother liquor is of higher total solids, animals do not have to ingest as much fluid to get the same nutritional benefit.

Operating at higher total solids in the evaporator and the crystallising stages also inhibits microbiological growth resulting in a better mother liquor compared to prior art.

In some embodiments the cooling crystalliser produces a mother liquor having a total solids content of at least about 35, 36, 37, 38, 39, 40, 41, 42, 43, 44, 45, 46, 47, 48, 49, 50, 51, 52, 53, 54 to 55% by weight lactose, and useful ranges may be selected between any of these values (for example, about 35 to about 55, about 35 to about 50, about 35 to about 46, about 35 to about 42, about 38 to about 55, about 38 to about 51, about 38 to about 47, about 38 to about 42, about 40 to about 55, about 40 to about 53, about 40 to about 49, about 42 to about 55, about 42 to about 54, about 42 to about 50, about 42 to about 48, about 45 to about 55, about 45 to about 51, about 45 to about 49, about 48 to about 55, about 48 to about 52% by weight lactose).

4. Crystal Washing

A washing process aims to reduce the impurities by washing the surface of the crystals.

In some embodiments the lactose crystals are washed from the decanter using a combination of saturated lactose solution and water.

In some embodiments the wash water is passed to a hydrocyclone to separate lactose crystals from the wash water. The lactose crystals separated from the wash water are recycled to the evaporation stage.

In some embodiments the washing process includes the additional steps of (1) agitation, (2) transference of the wash water to a hydrocyclone to separate the crystals from the wash water. After washing the lactose crystals are passed to a centrifuge and separated from the wash water.

5. Drying

In some embodiments the lactose crystals are dried. Various methods of drying can be used, for example, flash drying or liquidised bed drying.

Once dried, the product of the present invention comprises at least 95, 96, 97, 98 or 99% by weight of lactose crystals as alpha-lactose monohydrate. Additionally, the product has a total solids content of at least 99% by weight.

Various aspects of the invention will now be illustrated in non-limiting ways by reference to the following examples.

EXAMPLES

Example 1

Standard Lactose Crystallisation

A lactose-containing liquid is obtained as a by-product of cheese manufacture or casein manufacture. The lactose-containing liquid is ultrafiltered and the whey permeate (containing lactose and minerals) is concentrated by reverse osmosis to a total solids of 18-20% by weight. The concentration of lactose is approximately 80% of the total solids.

The lactose-containing fluid was further concentrated to 60% total solids in an evaporator.

The lactose-containing fluid was then transferred to a cooling crystalliser and processed using standard processes to commercial grade lactose.

We found that this process, producing 60% total solids. This leads to a theoretical loss of 7.6 units of lactose in mother liquor (based on lactose in solution at a solubility of 0.19 g lactose/g water (at 12° C.).

Example 2

Crystallising Evaporation

Crystallising evaporation is carried out as per the present invention.

A lactose-containing liquid is obtained as a by-product of cheese manufacture or casein manufacture. The lactose-containing liquid is ultrafiltered and the whey permeate (containing lactose and minerals) is concentrated by reverse osmosis to a total solids of 18-20% by weight. The concentration of lactose is approximately 80% of the total solids.

The whey permeate is then evaporated using a falling film evaporator at a temperature of 74-80° C. to a total solids concentration in the range of 58-62% by weight. The concentration of lactose is approximately 80% of the total solids.

The whey permeate is then passed into a crystallising evaporator that uses a flooded tube evaporator as the heat exchanger. The liquid has a dissolved lactose content of between 70 to 128 g per 100 g of water and the operating temperature of the crystallising evaporator is 65 to 70° C. The average residence time in the crystallising evaporator is about 3 hours and this results in the lactose-containing liquid having a total solids of about 70 to 74% by weight.

Therefore, this process results in higher total solids for crystallising in the cooling crystallisers.

We found the process was more stable due to the buffer time in the crystallising evaporator. Additionally we found the process was more stable due to the consistent crystal composition in the feed to the cooling crystalliser.

It is more stable than the traditional process because it seeds the cooling crystallisers with a consistent crystal. i.e. each batch feeds the cooling crystalliser with a consistent crystal size.

In this process a percentage of the stream is continuously bled off from the concentration process and sent to cooling crystallisers. This allows for more permeate to be feed into the process. A key part of this process is the use of hydro-cyclones at the point of bleeding off the concentrated material. The concentrated product is pumped into the hydro-cyclones and using centripetal force the larger crystals are separated from the smaller ones. It is these larger crystals that are sent to the cooling crystallisers, with the smaller ones being retained in the process to allow them further time for growth. The use of the hydro-cyclones allows the operation of a continuous process and increases the mean particle size produced.

The lactose-containing liquid is retained in the crystallising tanks for about 15 to about 30 hours where the final temperature of the crystal slurry is between 8 to 25° C.

Once the cooling process is complete the crystallised lactose is separated from the remaining solution using a decanter centrifuge. A slurry of mother liquor and crystals are pumped from the crystallisers into the decanter centrifuge and the crystals are spun off. The mother liquor is discharged and the crystals move forward in the process.

We also found that our process resulted in less lactose being lost in the mother liquor. For example, running our process up to 74% total solids means, with lactose in solution at a solubility of 0.19 g lactose/g water (at 12° C.), leads top a theoretical loss of 4.9 units of lactose in mother liquor, which is an improvement over standard processes. There are other considerations that impact for overall process yield such as crystal size and washing, but this example illustrates the fundamental advantage of obtaining high total solids when manufacturing lactose The crystals from the decanter are washed with water to remove impurities from the surface of the crystals.

Once the crystals are separated from the wash water they are then sent to the dryer so that the final moisture can be removed. This is done to ensure the crystals remain in a free flowing form and do not form a solid cake. Drying is carried out using a liquidised bed dryer to produce a product containing >99% by weight total solids.

Once a dry product is produced that meets customer requirements it is packed and stored. Packaging maybe either in 25 kg bags or in one tonne bulk bags, this is determined by customer requirements and end market uses.

Where in the foregoing description reference has been made to elements or integers having known equivalents, then such equivalents are included as if they were individually set forth.

Although the invention has been described by way of example and with reference to particular embodiments, it is to be understood that modifications and/or improvements may be made without departing from the scope or spirit of the invention.

We claim:

1. A method of crystallising lactose from a lactose-containing liquid comprising providing a lactose-containing liquid comprising less than 80% total solids by weight, providing an evaporator system that comprises a heat exchanger and an evaporation vessel, the heat exchanger comprising a tube or tubes that define a flowpath having an inlet and an outlet, heating the lactose-containing liquid in the heat exchanger to about 50 to about 90° C. such that the lactose-containing liquid passes along the flowpath by forced circulation or thermo-siphoning, concentrating the lactose-containing liquid in the evaporation vessel, to generate crystallised lactose in the lactose-containing liquid in the evaporator system.

2. The method of claim 1, wherein multiple crystallising evaporators are used in series.

3. The method of claim 1, wherein a volume of liquid in the evaporator system is at least half an hourly throughput volume of the liquid input into the system.

4. The method of claim 1, wherein the lactose-containing liquid in the evaporation system has an average residence time of at least 30 min.

5. The method of claim 1, wherein the lactose-containing liquid passes through the heat exchanger with a turbulent flow having a Reynolds number of 1,100.

6. The method of claim 1, wherein the lactose-containing liquid has a dissolved lactose content from about 1 to about 217 grams per 100 grams of water and a total solids content from about 58 to 80% by weight.

7. The method of claim 1, wherein the evaporation vessel has an inlet to receive heated lactose-containing liquid from the heat exchanger, and an outlet to re-circulate the lactose-containing liquid to the heat exchanger.

8. The method of claim 1, wherein the heat exchanger is a flooded tube heat exchanger.

9. The method of claim 1, wherein the lactose-containing liquid comprises from about 5 to about 62% total solids by weight.

10. The method of claim 1, wherein the lactose-containing liquid comprises from about 5 to about 24% total solids by weight, that is further concentrated to about 55 to about 62% by weight total solids for transfer to the crystallising evaporator.

11. The method of claim 1, wherein the crystallised lactose-containing liquid has a total solids content of from about 58 to about 74% by weight.

12. The method of claim 1, wherein after sufficient lactose crystal growth has occurred in the evaporation vessel, the concentrated lactose-containing liquid, having a total solids content of from about 58 to about 80% by weight, is transferred to a cooling crystalliser.

13. The method of claim 1, wherein after sufficient lactose crystal growth has occurred in the evaporation vessel, the concentrated lactose-containing liquid, having a total solids content of from about 65 to about 80% by weight, is transferred to a cooling crystalliser.

14. The method of claim 1, wherein the crystals in the crystallising evaporator are homogeneously distributed.

15. The method of claim 1, wherein at least 90% of the lactose crystals by weight eluting from the crystallising evaporator have a particle size of at least 90, 100, 110, 120, 130, 140, 150, 160, 170, 180, 190 or 200 microns in diameter.

16. The method of claim 1, wherein at least 50% of the lactose crystals by weight eluting from the crystallising evaporator have a particle size of at least 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 microns in diameter.

17. The method of claim 1, wherein at least 10% of the lactose crystals by weight eluting from the crystallising evaporator have a particle size of at least 500, 550, 600, 650, 700, 750, 800, 850, 900, 950 or 1,000 microns in diameter.

18. The method of claim 1, wherein after sufficient residence time in the evaporation vessel, a portion of lactose-containing liquid is recirculated to the evaporator system and the concentrated lactose-containing liquid that remains is transferred to a cooling crystalliser.

19. The method of claim 12, wherein the cooling crystalliser produces a mother liquor having a total solids content of from about 35 to 55% by weight lactose.

20. The method of claim 12, wherein the lactose-containing liquid that is transferred to a cooling crystalliser is classified by particle size.

21. The method of claim 20 wherein a hydrocyclone is used to classify the lactose-containing liquid into a first liquid that is recirculated to the evaporator system and a second liquid that is transferred to a cooling crystalliser.

22. The method of claim 21 wherein the hydrocyclone classifies the lactose-containing liquid into two streams of lactose-containing liquid, the first stream is recirculated to the evaporator system and the second stream having lactose crystals of larger average size than the first stream, and wherein the second stream is transferred to a cooling crystalliser.

23. The method of claim 1, wherein the heat exchanger is a rising film heat exchanger.

* * * * *